(12) United States Patent
Yamamori et al.

(10) Patent No.: US 6,218,665 B1
(45) Date of Patent: Apr. 17, 2001

(54) INFRARED DETECTOR AND GAS ANALYZER

(75) Inventors: Shinji Yamamori; Hidetoshi Dainobu, both of Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 09/126,604

(22) Filed: Jul. 31, 1998

(30) Foreign Application Priority Data

Jul. 31, 1997 (JP) .................................................. 9-206003

(51) Int. Cl.[7] .................................................. G01N 21/61
(52) U.S. Cl. .................. 250/343; 250/341.5; 250/339.09
(58) Field of Search .................................... 250/343, 345, 250/346, 341.5, 338.3, 339.09, 338.4

(56) References Cited

U.S. PATENT DOCUMENTS

| 4,596,931 | * | 6/1986 | Ehnholm et al. | 250/343 |
|---|---|---|---|---|
| 5,070,244 | * | 12/1991 | Simpson | 250/343 |
| 5,153,436 |  | 10/1992 | Apperson et al. . |  |
| 5,341,214 | * | 8/1994 | Wong | 356/437 |
| 5,693,945 | * | 12/1997 | Akiyama et al. | 250/345 |

FOREIGN PATENT DOCUMENTS

| 0 385 256 | 9/1990 | (EP) . |
| 0 733 341 | 9/1996 | (EP) . |
| WO 88/02889 | 4/1988 | (WO) . |

OTHER PUBLICATIONS

Patent Abstracts of Japan vol. 096 No. 009, Sep. 30, 1996 & JP 08 122254 A (Horiba LTD) May 17, 1996 *Abstract.

* cited by examiner

*Primary Examiner*—Constantine Hannaher
*Assistant Examiner*—Albert Gagliaroi
(74) *Attorney, Agent, or Firm*—Sughrue, Mion, Zinn, Macpeak & Seas, PLLC

(57) ABSTRACT

When first and second PbSe detectors 6 and 7 are irradiated with intermittent infrared radiation from a light source 3, infrared radiation detection circuits 21a and 21b output electrical signals in accordance with the magnitude of the infrared radiation, respectively. The output signals are supplied as they are to a CPU 32 via A/D converter 31, and, on the other hand, AC signals of the output signals via AC components detection circuits 22a and 22b reach the CPU 32. The CPU 32 corrects the AC signals, based on data which relates to the resistances and sensitivities of the PbSe detectors 6 and 7 and which are stored in an EEPROM 23, and the DC components of the output signals of the infrared radiation detection circuits 21a and 21b.

10 Claims, 10 Drawing Sheets

| TEMPERATURE °C | DARK RESISTANCE (kΩ) | RELATIVE SENSITIVITY (NORMALIZED TO 1 AT 20°C) |
|---|---|---|
| 0 | 3294 | 1.211 |
| 10 | 2461 | 1.111 |
| 20 | 1875 | 1.000 |
| 30 | 1447 | 0.8727 |
| 40 | 1130 | 0.7495 |

INFRARED DETECTOR AND GAS ANALYZER

BACKGROUND OF THE INVENTION

1. Field of the Invention

The present invention relates to an infrared detector using a photoconductive infrared detector, and also to a gas analyzer having the configuration of such an infrared detector.

2. Related Art

As a device which measures the concentration of carbon dioxide in a respiratory gas, known is a non-dispersive infrared analyzer. A carbon dioxide analyzer using the principle of the device is disclosed in U.S. Pat. No. 5,153,436.

The non-dispersive infrared analyzer measures a gas concentration such that an infrared radiation through the gas to measure an amount of attenuation of the infrared radiation in wavelength absorbed by the gas. In U.S. Pat. No. 5,153,436, in order to increase the measurement accuracy, there is employed two infrared radiation detectors. The light passing through an airway adapter for guiding a respiratory gas is divided in two lights by a beam splitter. A light reflected from the bean splitter is guided to a first PbSe detector via an optical filter. This filter allows to pass a light having a band of approximately 4.3 $\mu$m which is absorbed by carbon oxide gas.

A light passing through the beam splitter is guided to a second PbSe detector via an optical filter different from the optical filter located in the first PbSe detector. This filter allows to pass a light having a band of approximately 3.7 $\mu$m which is not absorbed by carbon dioxide gas.

Assuming that output signal Vs represents the amount of the infrared light guided into the first PbSe detector and output signal Vr represents the amount of the infrared light guided in to the second PbSe detector, the gas concentration can be detected without being affected by a drift due to variation of infrared radiation of the light source, by calculating a ratio of VS/VR.

Even when the ratio of VS/VR is obtained in this way, the temperature drift remains to affect the detection because the first and second PbSe detectors are different from each other in temperature coefficient of the sensitivity. In the conventional art, therefore, the temperatures of PbSe detectors are controlled by using heaters and thermistors.

In the conventional art, as described above, heaters, thermistors, and a temperature control circuit are necessary in order to maintain a photoconductive infrared detector at a constant temperature. Therefore, there arise problems in that the production cost is high, that the power consumption is increased, and that the warm-up period is prolonged.

SUMMARY OF THE INVENTION

It is an object of the invention to provide an infrared detector unit in which means for maintaining a photoconductive infrared detector at a constant temperature is not required and the temperature drift of the detector is corrected, and a gas analyzer having the configuration of such as infrared detector unit.

According to an aspect of the present invention, there is provided the infrared detector comprising:

a light source which intermittently generates infrared radiation;

signal outputting means having a photoconductive infrared detector which is irradiated with the infrared radiation from the light source via a measurement object, and for outputting an electric signal which corresponds to a resistance of the photoconductive infrared detector;

alternating current AC (alternating current) component detecting means for detecting an AC component from the output signal of the signal outputting means;

storage means for storing data specific to the photoconductive infrared detector, the data relating to the resistance and a sensitivity; and correcting means for correcting that AC component detected by the AC component detecting means, based on the data stored in the storage means and a DC (direct current) component of the signal output from the signal outputting means.

According to another aspect of the present invention, the measurement object is a gas body containing carbon dioxide.

According to another aspect of the present invention, the photoconductive infrared detector is a lead selenide (PbSe) detector.

In this configuration, the resistance of the photoconductive infrared detector is varied in accordance with the magnitude of the radiation impinging on it. The signal outputting means outputs an electric signal which corresponds to the resistance. The AC component of the output signal of the signal outputting means is detected by the AC component detecting means. The AC component corresponds to the magnitude of the radiation which intermittently impinges on the detector via the measurement object. The correcting means corrects the AC component, based on the data stored in the storage means and the DC component of the signal output from the signal outputting means.

According to another aspect of the present invention, gas concentration calculation means for calculating a concentration of the designated gas, based on the AC component corrected by the correcting means.

DETAILED DESCRIPTION OF THE PREFERRED EMBODIMENTS

Figure 13:
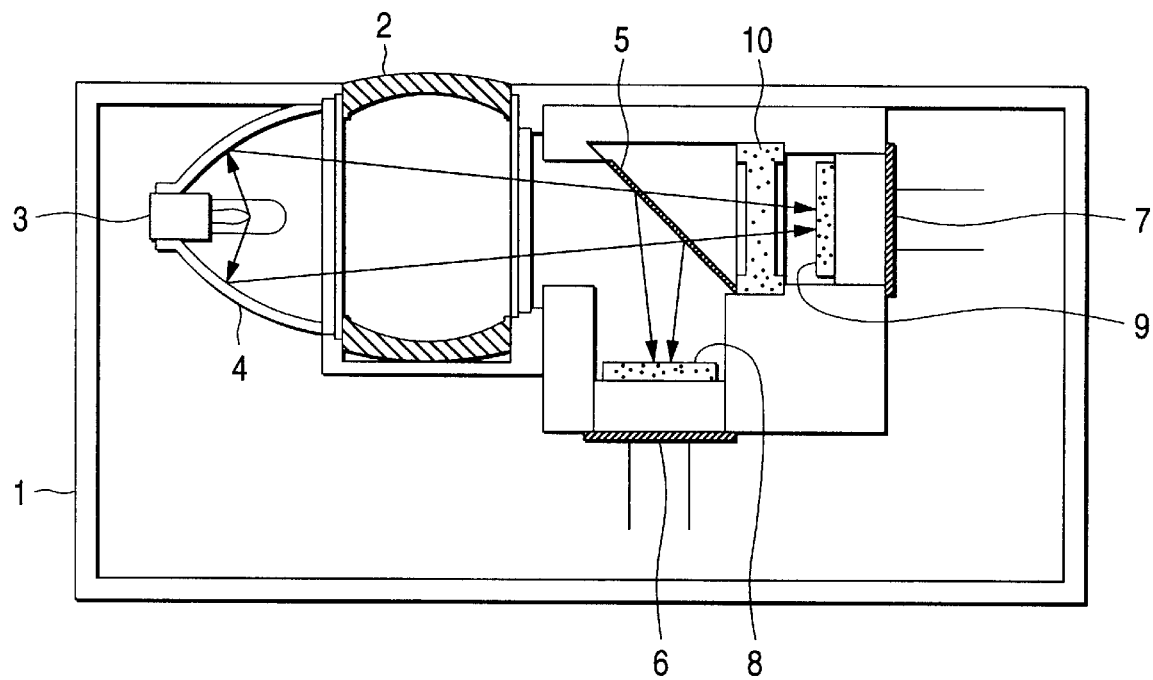
FIG. 13 is a view showing the configuration of a sensor section of the embodiment of the invention.
Figure 14:
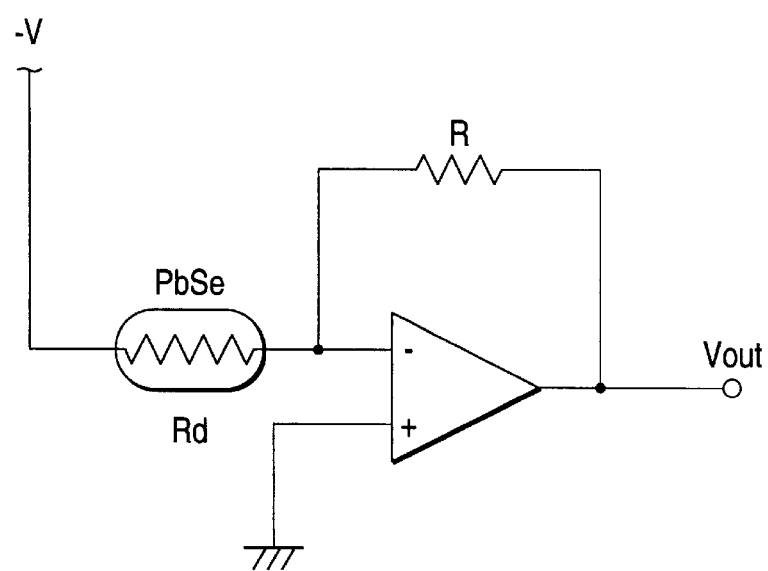
FIG. 14 is a view showing an example of an infrared radiation detection circuit using a PbSe detector.

A first embodiment of the invention will be described. FIG. 13 shows the structure of a sensor section of the analyzer of the present invention. As shown in the figure, in a case 1, disposed are an airway adapter 2 which guides a respiratory gas, an emitter 3 and a mirror 4 which cooperate with each other to irradiate the airway adapter 2 with infrared radiation; and a beam splitter 5 which allows part of the infrared radiation passing through the airway adapter to pass through the beam splitter 5 and reflects the remaining part in the other direction. The infrared radiation reflected from the bean splitter 5 is guided to a first lead selenide (PbSe) detector 6, and the infrared radiation passing through the beam splitter 5 is guided to a second PbSe detector 7. Bandpass filters 8,9 which allow a narrow band of infrared radiation centered at a wavelength of 4.3 $\mu$m are disposed in front of the first and second detector 6,7. The wavelength of 4.3 $\mu$m is strongly absorbed by carbon dioxide. Carbon dioxide gas cell 10 having windows such that infrared radiation passes therethrough is disposed between the beamsplitter 5 and the second PbSe detector 7. A strong bsorption is caused by carbon dioxide of high concentration filled in the gas cell 10 so that even if the concentration of carbon dioxide passing through airway adaptor 2 is changed largely, the change of the amount of the infrared radiation reached to the second PbSe detector 7 is very small. The first and second PbSe detectors 6 and 7 are incorporated into detection circuits shown in FIG. 14, respectively. A PbSe detector is a detector in which the resistance is varied by irradiation of infrared radiation. When each of the PbSe detectors is irradiated with intermittent infrared radiation, therefore, the AC signal of the output voltage of the detection circuit corresponds to the magnitude of the infrared radiation impinging on it.

Figure 2:
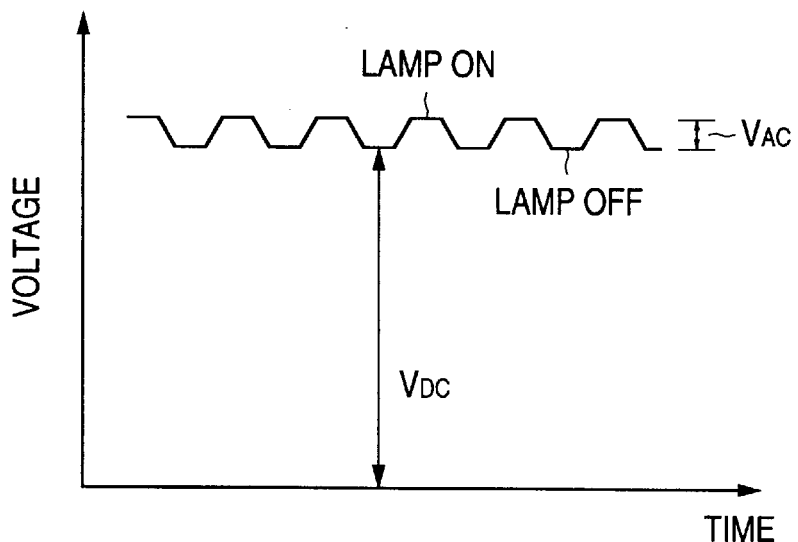
FIG. 2 is a view showing output signals of infrared radiation detection circuits 21a and 21b shown in FIG. 1.
Figure 3:
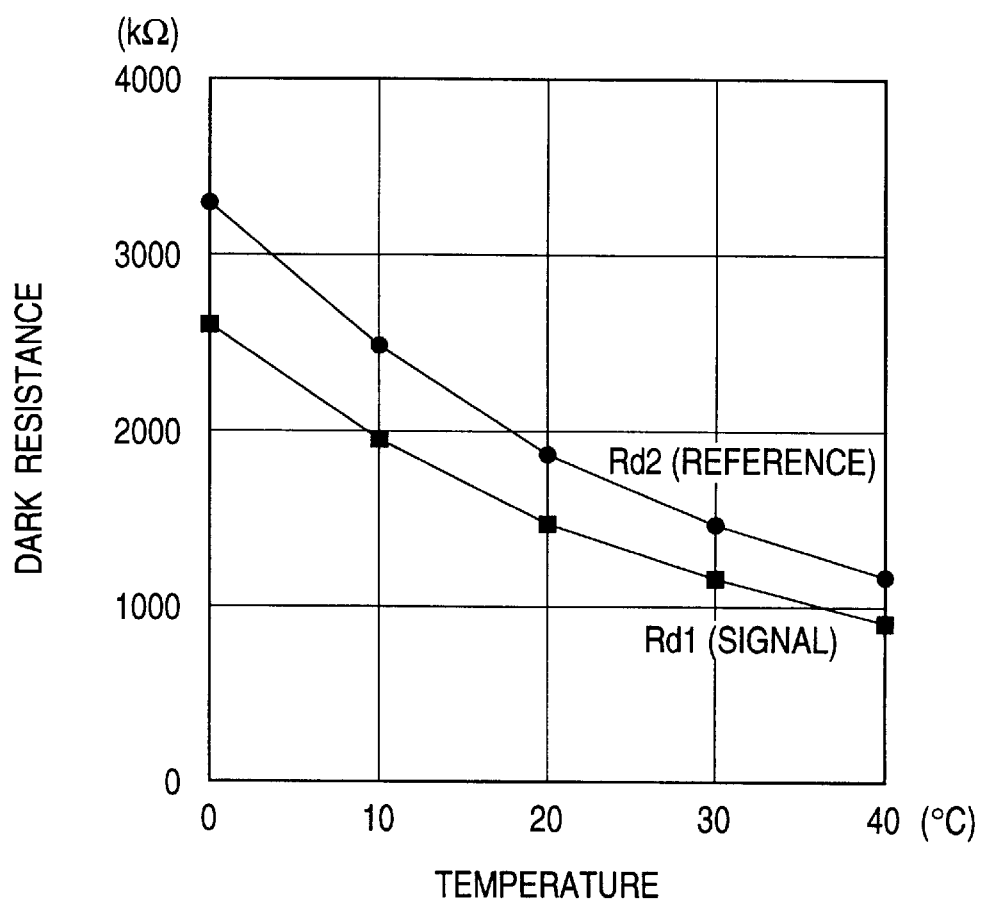
FIG. 3 is a view showing relationships between the temperature and the dark resistance of a PbSe detector.

And then, the principle of the embodiment will be described. As described above, a PbSe detector is a photoconductive infrared detector in which the resistance is varied by irradiation of infrared radiation. The resistance is largely varied also by temperature variation. In accordance with a variation of the resistance, also the sensitivity is varied. In a measurement of this kind, usually, two detectors are used, on the of the detectors is used as a signal detector (Signal), and the other detector is used as a reference detector (Reference). The relationships between the dark resistance (the resistances Rd1 and Rd2 appearing when the detectors are not irradiated with light) of the detectors and the temperature vary depending on the detectors. As shown in FIG. 3, each of the relationships is uniquely determined. When the dark resistance Rd1 or Rd2 is measured, therefore, it is possible to know the temperature of the corresponding detector. In the case where the detection circuit has the configuration shown in FIG. 14 and a PbSe detector is irradiated with infrared radiation which is intermitted by a chopper or the like, an output Vout shown in FIG. 2 is obtained. The dark resistance Rd can be obtained by the following expression:

$$Rd = VR/VDC \text{ (}V\text{: constant)} \tag{1}$$

Where VDC is the DC (Direct Current) signal when the detector is not irradiated with infrared radiation.

Since the PbSe detector is intermittently irradiated with infrared radiation, an AC signal of an amplitude VAC which is proportional to the magnitude of the infrared radiation as shown in FIG. 2 is obtained.

Figure 4:
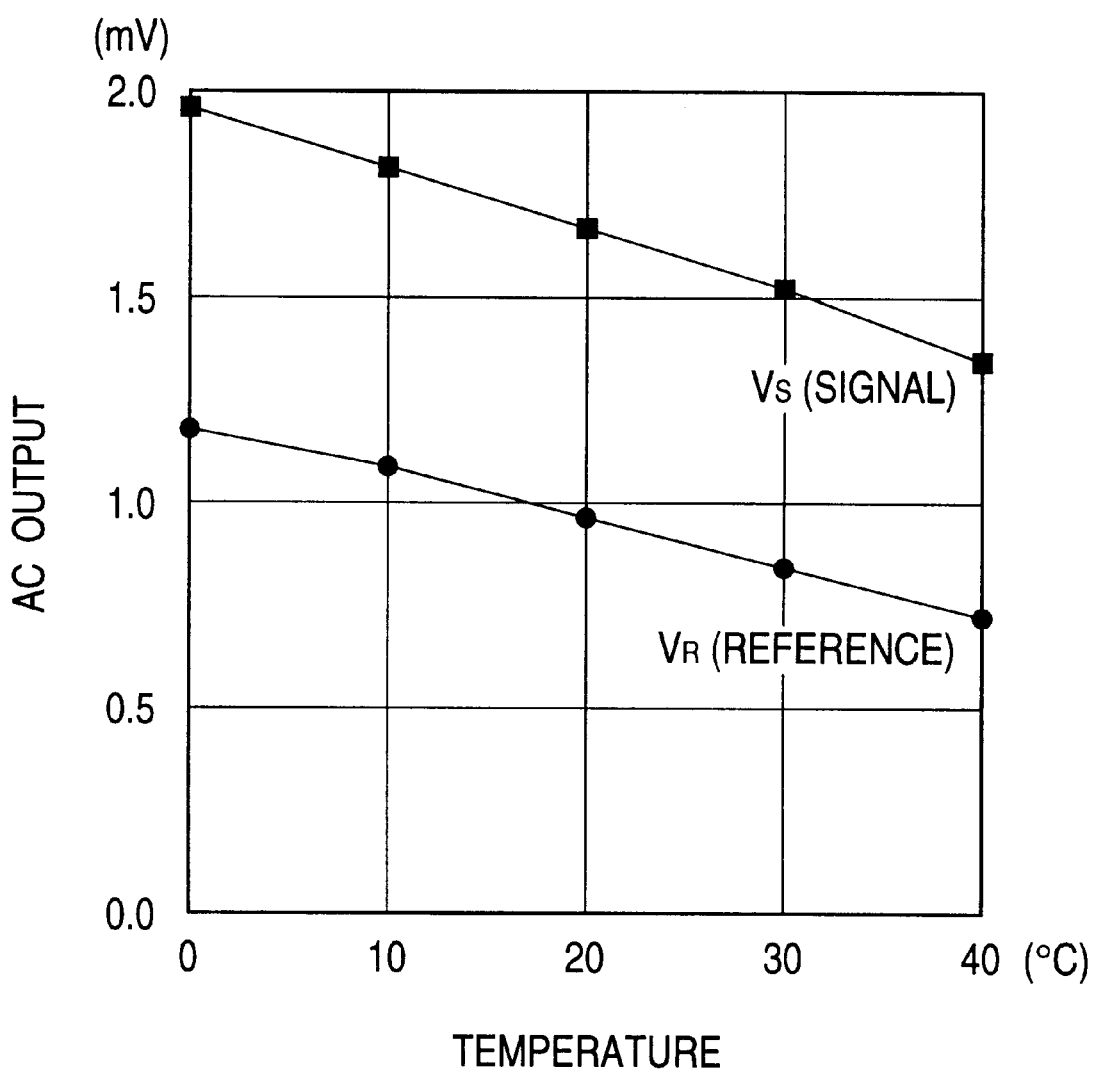
FIG. 4 is a view showing relationships between the temperature and an AC output of a detector in an infrared radiation detection circuit using a PbSe detector.
Figures 5, 6:
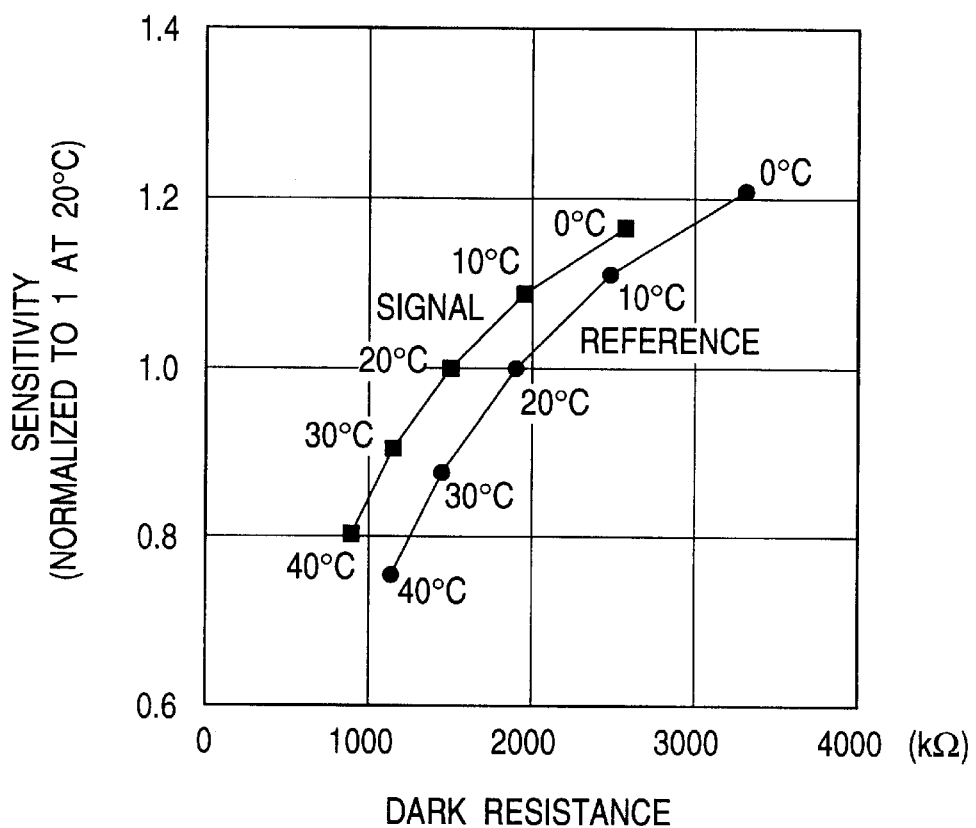
FIG. 5 is a view showing relationships between the dark resistance and the sensitivity of a detector in the infrared radiation detection circuit using a PbSe detector.
FIG. 6 is a view showing an example of the contents of an EEPROM 23 shown in FIG. 1.

FIG. 4 shows the relationships between the amplitudes VS and VR of alternating currents of the two detection circuits and the temperature under conditions that the amount of infrared radiation is constant. FIG. 5 shows the relationships between the dark resistance and the sensitivity. These relationships are previously measured for each detector. In the embodiment, the sensitivity means the amplitude of the AC in the case where the amplitude of the AC at 20C is standardized as 1.

When the value VDC of the DC signal is obtained, it is possible to obtain the dark resistance Rd. From the dark resistance, the temperature can be known, and the sensitivity can be obtained from the temperature. Based on the sensitivity, the value of the AC signal can be corrected to the value obtained when the detector is at 20C.

Figure 1:
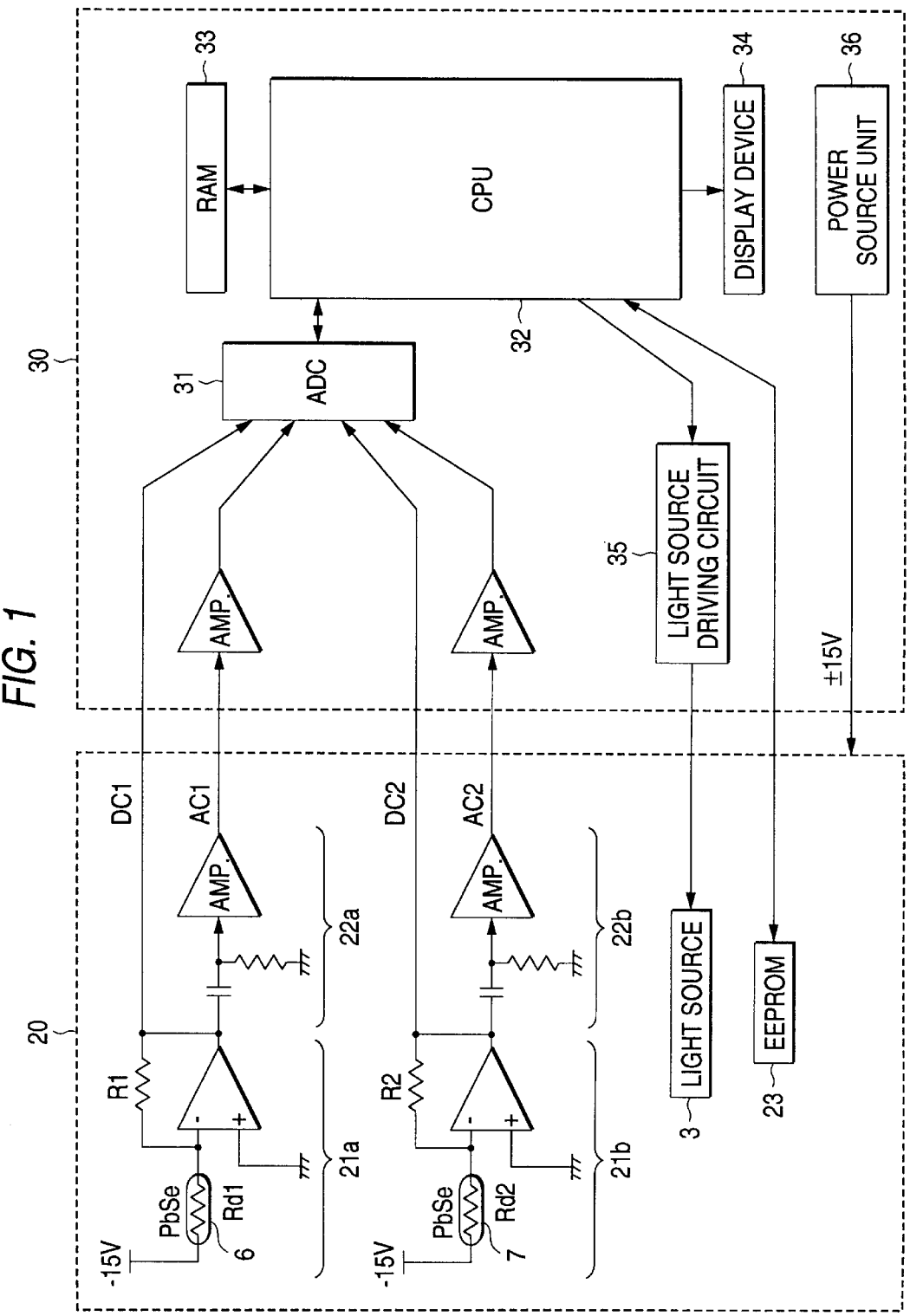
FIG. 1 is a block diagram showing the configuration of an embodiment of the invention.

FIG. 1 is a block diagram of a carbon dioxide analyzer using the principle described above. As shown in the figure, the analyzer consists of a sensor section 20 and a main section 30. In the sensor section 20 shown in FIG. 1, only electric circuit components are illustrated. The mechanical components of the senor section 20 are configured in the same manner as those shown in FIG. 11, and hence their description is omitted.

The electric circuit components of the sensor section 20 will be described. The sensor section 20 comprises: an infrared radiation detection circuit 21a having the first PbSe detector 6; an AC component detection circuit 22a which detects the AC component from the output signal of the infrared radiation detection circuit 21a; an infrared radiation detection circuit 21b having the second PbSe detector 7; an AC component detection circuits 22b which detects the AC component from the output signal of the infrared radiation detection circuit 21b; the light source 3; and an EEPROM 23.

The infrared radiation detection circuit 21a consists of the first PbSe detector 6, an operational amplifier, and a resistor. A constant voltage of −15 volts is applied to one end of the first PbSe detector 6. The other end of the detector is connected to the inverting input terminal of the operational amplifier. The noninverting input terminal of the operational amplifier. The noninverting input terminal of the operational amplifier is grounded. The inverting input terminal and the output terminal of the operational amplifier are connected to each other via the resistor (having the resistance R1). The infrared radiation detection circuit 21b is configured in the same manner (the resistor in this circuit has the resistance R2).

Each of the AC component detection circuits 22a and 22b consists of a high-pass filter composed of a capacitor and a resistor, and an amplifier which amplifies the output of the filter.

The relationships among the temperature, the dark resistance, and the relative sensitivity of each of the PbSe detectors used in the analyzer, i.e., the first and second PbSe detectors 6 and 7 are previously written into the EEPROM 23. FIG. 6 shows an example of such relationship. These values are previously obtained by measurements using a temperature constant chamber, etc. Furthermore, information relating the concentration of carbon dioxide to the rations of the outputs (outputs obtained when the temperature of each detector is 20C) of the two infrared radiation detection circuits 21a and 21b, and the resistance R1 and R2 used in Ex. (1) are written into the EEPROM 23.

The light source 3 is a lamp which irradiates infrared radiation.

The main section 30 comprises: an A/D converter 31 which converts signals directly supplied from the infrared radiation detection circuits 21a and 21b of the sensor section 20, and those supplied from the infrared radiation detection circuits 21a and 21b of the sensor section 20 via the amplifiers, into digital signals; and a CPU (Central Processing Unit) 32 which process data and controls various portions, based on the signals supplied from the A/D converter 31, and the data stored in the EEPROM 23 of the sensor section 20. The main section 30 further comprises: a RAM 33 which is used by the CPU 32 is read and write data during data processing; a display device 34 on which a result of the data processing performed by the CPU 32 is displayed; a light source driving circuit 35 which drives the light source 3 in accordance with instructions from the CPU 32; and a power source circuit 36 which powers the portions of the main section 30 and the sensor section 20.

Wire lead through which the main section 30 and the sensor section 20 are connected to each other are bundled into a single cable.

In the embodiment, the infrared radiation detection circuits 21a and 21b correspond to the signal outputting means, the AC component detection circuits 22a and 22b correspond to the AC component detecting means, the EEPROM 23 corresponds to the storage means, the function of the CPU 32 for correcting the AC component corresponds to the correcting means, and the function of the CPU 32 for obtaining the concentration of carbon dioxide corresponds to the gas concentration calculation means.

Figure 7:
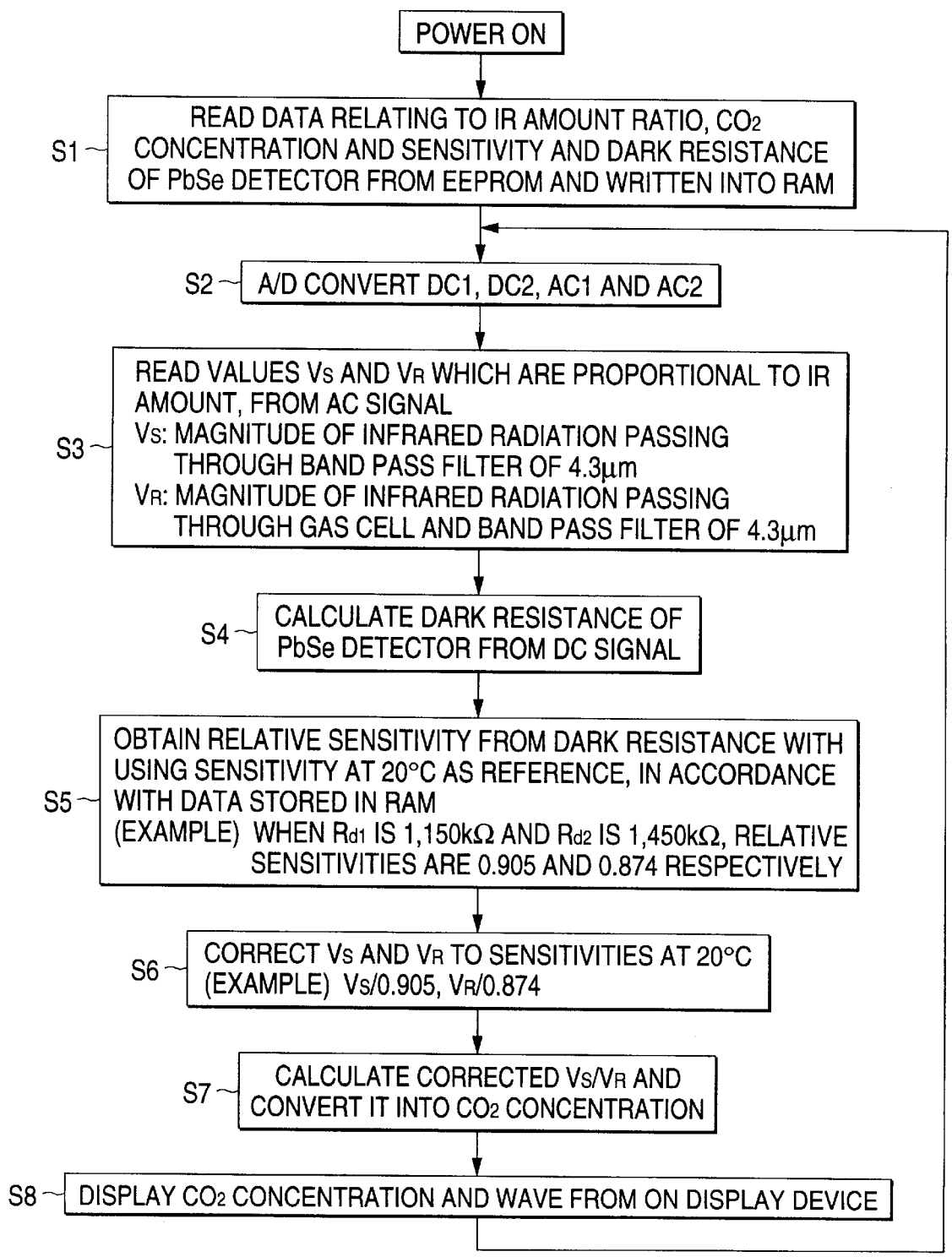
FIG. 7 is a view illustrating the operation of the first embodiment of the invention.

The operation of the thus configured analyzer will be described with reference to the flowchart of FIG. 7.

When the analyzer is powered ON, the CPU 32 reads out the data stored in the EEPROM 23 and writes the data into the RAM 33 (S1). Then, the CPU 32 gives the light source driving circuit 35 instructions to start the operation, so that the light source 3 pulsatively emits light at 37 Hz.

The infrared radiation emitted from the light source 3 passes through the airway adapter 2, and then divided into two parts by the bean splitter 5. One of the parts passes through the bandpass filter 8 and then enters the first PbSe detector 6, and the other part passes through the carbon dioxide cell 10 and the bandpass filter 9 and then enters the second PbSe detector 7.

The output of the infrared radiation detection circuits 21a is supplied as a direct current (DC) signal DC1 to the A/D converter 31. On the other hand, the output is also subjected to extraction of the AC component in the AC component detection circuit 22a, and an AC signal AC1 of the output is supplied to the A/D converter 31. The output of the infrared radiation detection circuits 21b is processed in the same manner, so that a DC signal DC2 and an AC signal AC2 are supplied to the A/D converter 31. The A/D converter 31 digitizes these supplied signals (S2).

The CPU 32 then reads the amplitudes VS and VR of the AC signals AC1 and AC2 which have been digitized by the A/D converter 31, and stores the amplitudes in the RAM 33 (S3).

Next, the CPU 32 reads the values VDC1 and VDC2 of the DC signals DC1 and DC2 which have been digitized by the A/D converter 31. The data resistances Rd1 and Rd2 of the PbSe detectors are calculated from these values and Equation. (1) above (S4).

From the calculated dark resistances, the CPU 32 obtains the relative sensitivities of the PbSe detectors with reference to the table stored in the RAM 33 (S5).

By using the obtained relative sensitivities, the CPU 32 corrects the amplitudes VS and VR of the AC signals which are read in step S3, to values at 20C (S6).

The CPU 32 calculates the ratio of corrected VS and VR, and obtains the concentration of carbon dioxide, on the basis of the data stored in the RAM 33 (S7).

The CPU 32 displays the obtained concentration of carbon dioxide on the display device 34 (S8), in the form of a numeric value or a waveform.

Figure 8:
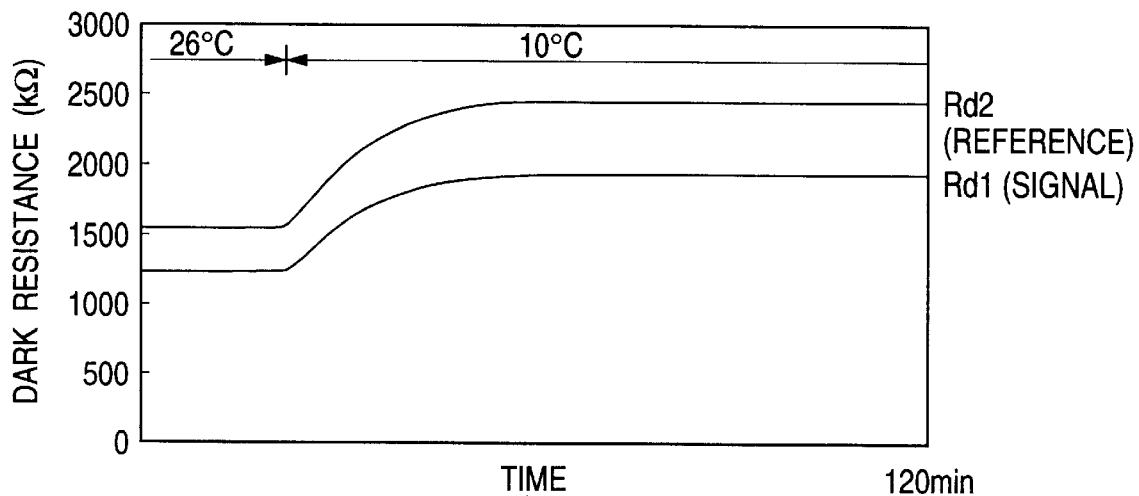
FIG. 8 is a view illustrating effects of the embodiment of the invention.
Figure 9:
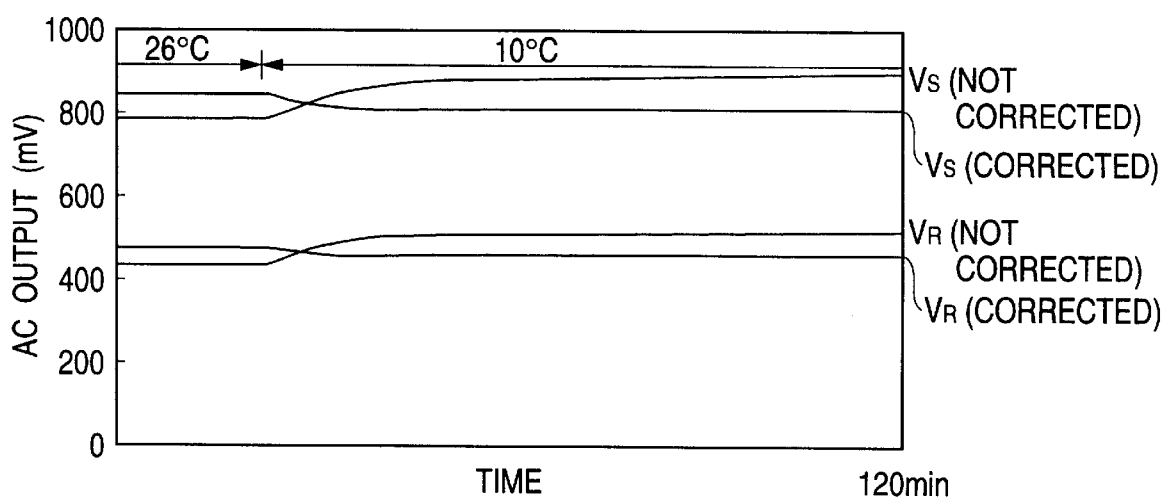
FIG. 9 is a view illustrating effects of the embodiment of the invention.
Figure 10:
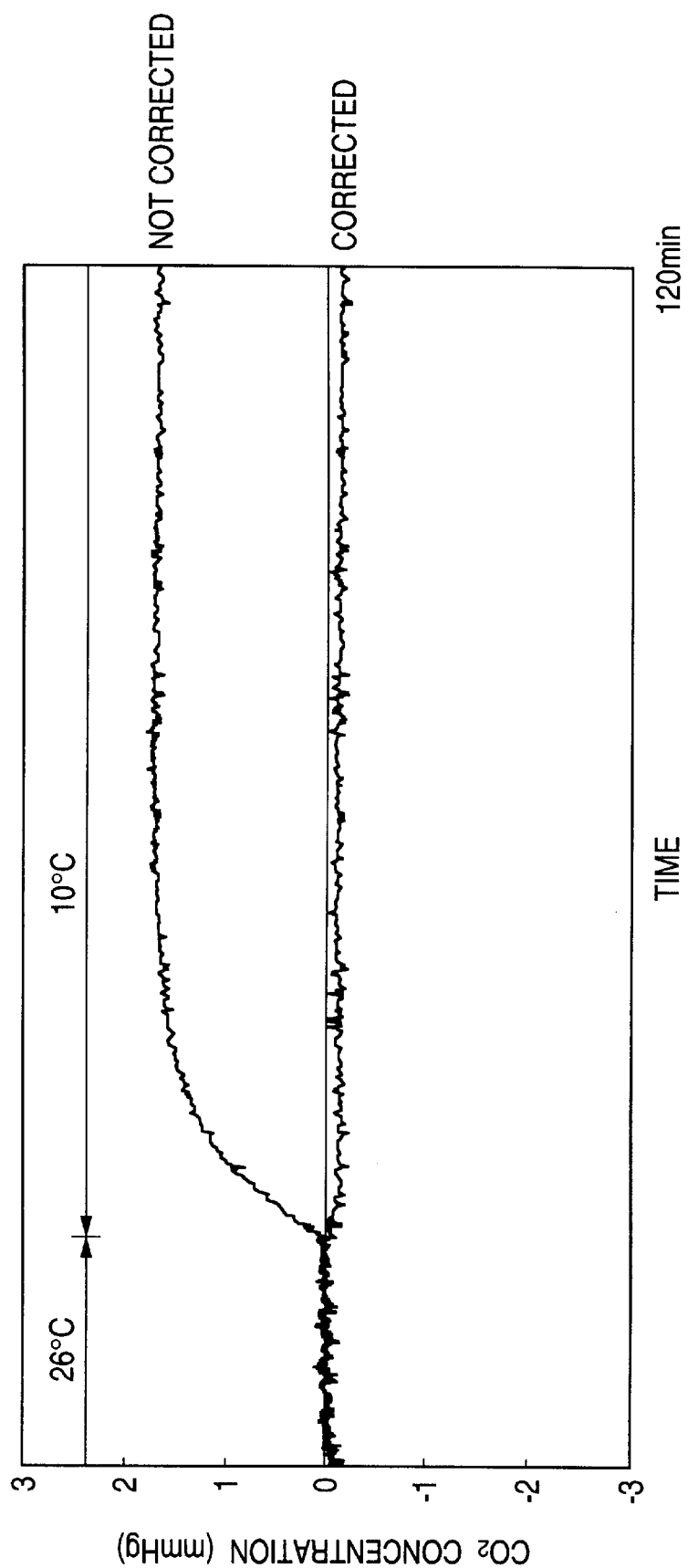
FIG. 10 is a view illustrating effects of the embodiment of the invention.

The sensor section of the analyzer was actually moved from room temperature (26C) into a temperature constant chamber at 10C. Then, results shown in FIGS. 8 to 10 were obtained. Specifically, the dark resistances and the AC signals of the detectors started to drift immediately after the sensor section was placed in the temperature constant chamber (FIGS. 8 and 9). By contrast, when the AC signals were corrected, the drift levels were reduced (FIG. 9). When a ratio of the signals is calculated and them converted into the concentration of carbon dioxide, the temperature drift is substantially eliminated (FIG. 10). From the above, it is confirmed that the temperature control on the PbSe detectors is not required and a measurement which is extremely stabilized is enabled.

In the embodiment, the resistance (dark resistances) Rd1 and Rd2 of the detectors are obtained from the DC signals VDC1 and VDC2 by using Equation. (1), the temperatures of the detectors are determined on the basis of the resistances, and the relative sensitivities at the temperature are obtained with reference to the table of FIG. 6 (steps S4 and S5 shown in FIG. 7). Alternatively, since the resistances R1 and R2 which are used in Equation. (1) are constant (known), a table which directly correlates the DC signals VDC1 and VDC2 at each temperature with the relative sensitivities may be previously prepared, and the table may be stored in the EEPROM 23. When such a table is used, the relative sensitivities are directly obtained from the DC signals VDC1 and VDC2. Therefore, it is not required to calculate Equation. (1) during the measurement, and hence the processing can be rapidly performed.

In the above example, the relative sensitivities are obtained by using a table. Alternatively, the relative sensitivities may be obtained in the following manner. An approximate expression indicating the relationships between the dark resistances Rd1 and Rd2 and the relative sensitivities, or that indicating the relationships between the DC signals VDC1 and VDC2 and the relative sensitivities is stored in the EEPROM 23, and the relative sensitivities are obtained by using the approximate expression.

Next, the second embodiment of the present invention will be described. The dark resistance could be calculated by Equation (1) using VDC at one of PeSe detectors 6 and 7, namely, the output voltage without irradiating the infrared irradiation.

Moreovers, as shown in FIG. 3, there is already known the relationship between the temperature and each of dark resistor of PbSe detectors 6 and 7, respectively so that the temperature of PbSe detector can be obtained. At this time, both PbSe detectors 6 and 7 are closely located. Thus, the temperature of both detectors are almost the same. Therefore, the temperature calculated by detecting by measurement of VDC1 or VDC2 could be considered to the temperature of both PbSe detectors.

Figure 11:
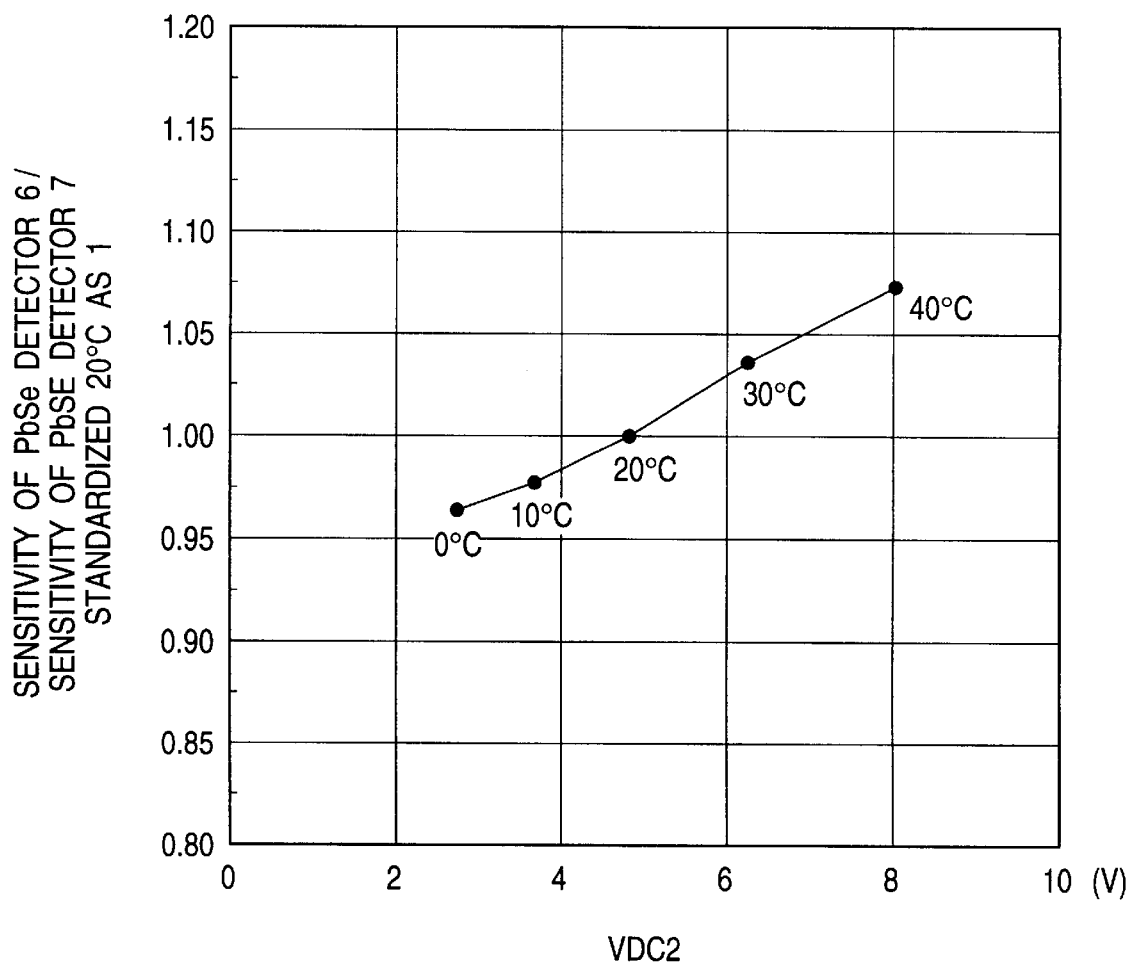
FIG. 11 is a view showing relationships between DC output of the second PbSe detector and the ratio of the two sensitivity of the first and second detector.

On the other hand, as shown in FIGS. 5 and 6, relative sensitivity defined between each temperature of PbSe detectors 6 and 7 (standardized data at 20° C. as 1) is known. Thus, the ratio of the two relative sensitivity is also known. FIG. 11 shows the relationship between VD2 and the ratio of the two relative sensitivity so that it is possible to correct VS/VR. Thus, the ratio of the two sensitivity could be directly calculated by use of one of direct current VCD1 or VDC2. Further, ratio VS/VR is directly corrected by using the VDC2.

Figure 12:
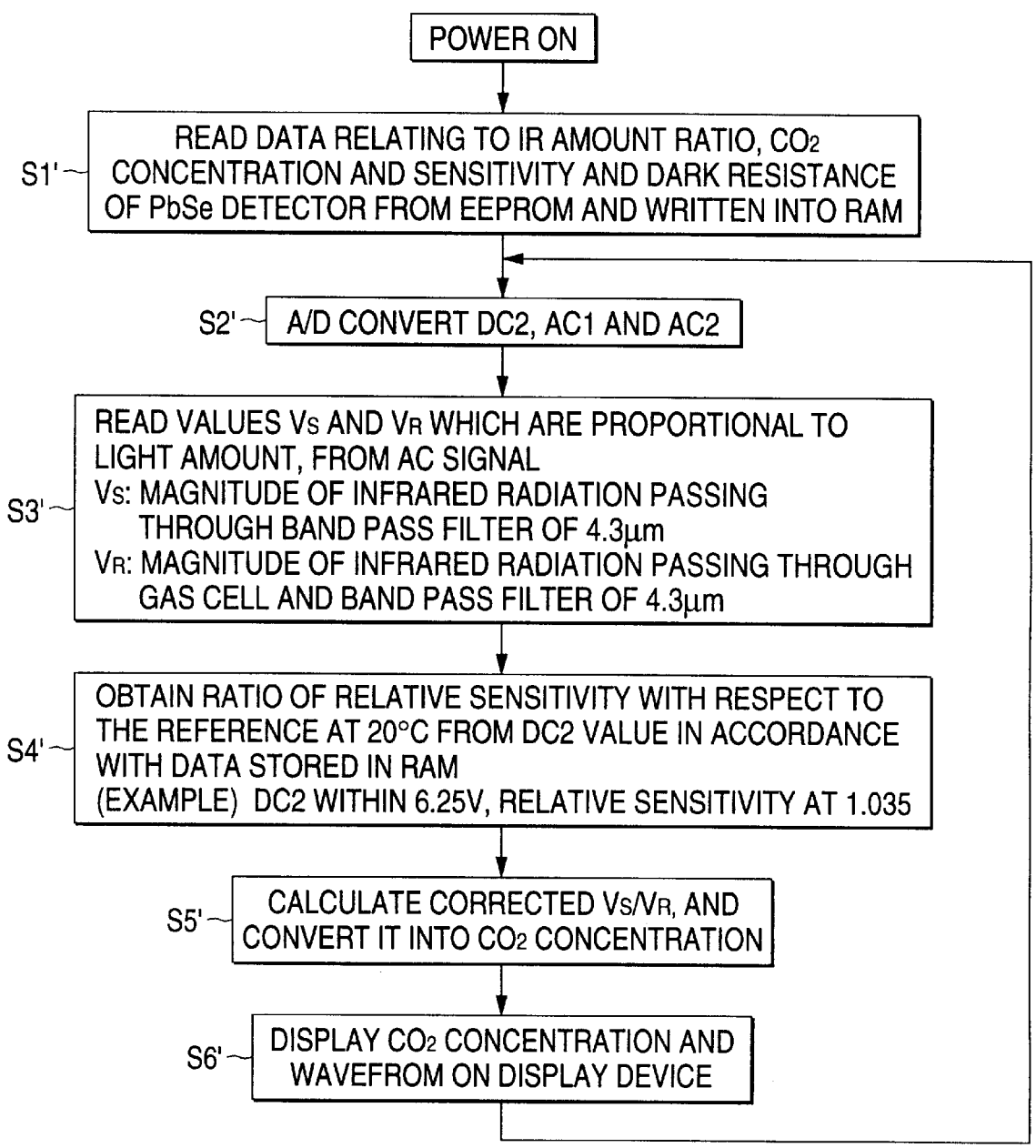
FIG. 12 is a view illustrating the operation of the second embodiment of the invention.

Next, the operation of the second embodiment will be described in view of the flowchart of FIG. 12.

When the analyzer is powered ON, the CPU 32 reads out the data stored in the EEPROM 23 and writes the data into the RAM 33 (S1'). The drive of the light source and the irradiation of infrared light are same as first embodiment.

The output of the infrared radiation detection circuit 21a is supplied as a direct current signal DC2 to the A/D converter 31. On the other hand, the output is also subjected to extraction of the AC component in the AC component detection circuit 22a, and an AC signal AC1 of the output is supplied to the A/D converter 31. The output of the infrared radiation detection circuits 21b is processed in the same manner, so that a DC signal DC2 and an AC signal AC2 are supplied to the A/D converter 31. In this step, the necessity signal of the DC component for calculating is one of VDC1 or VDC2. In this case, the necessity signal is VDC2. Thus, it is unnecessary to digitized signal VDC1 by A/D converter 31 (S2').

The CPU 32 then reads the amplitudes VS and VR of the AC signals AC1 and AC2 which have been digitized by the A/D converter 31, and stores the amplitudes in the RAM 33 (S3').

Next, the CPU 32 reads the value VDC2 of the DC signal DC2 which have been digitized by the A/D converter 31. From DC2, CPU32 obtains the ratio of the two relative sensitivity with reference to the table stored in the RAM 33 (S4').

By using the obtained the ratio of the two relative sensitivities, the CPU 32 corrects the ratio of VS/VR which are read in step S3', to values at 20C. (S5') to obtain the concentration of carbon dioxide.

The CPU 32 displays the obtained concentration of carbon dioxide on the display device 34 (S6), in the form of a numeric value or a waveform.

In this embodiment, as compared with the first embodiment, the number of steps in this embodiment is smaller than that of the first embodiment.

In the embodiment, one of the parts of infrared radiation which are divided by the beam splitter is allowed to pass through the carbon dioxide gas cell, and the two infrared radiation detection circuits detect infrared radiation of the same wavelength. Even where a water layer is formed on the window of the airway adapter, therefore, the measurement result is not affected by the formation. Consequently, an anti-fogging film can be used on the window of the airway adapter instead of sapphire as expensive material and the device is free from the heater, thereby attaining effects such as that the production cost can be lowered.

The invention may be similarly applied also to a device using infrared radiation of two wavelengths, such as that disclosed in U.S. Pat. No. 5,153,436 wherein one of two parts of infrared radiation which are divided by a beam splitter is detected of a bandpass filter which allows narrow band of the wavelength of infrared radiation absorbed by the measurement object gas to pass through, and the other part is detected via bandpass filter which allows narrow band of the wavelength of infrared radiation not absorbed by the measurement object gas to pass through. Specifically, in this case also, two photoconductive infrared detectors are used. When outputs of detection circuits into which the detectors are respectively incorporated are corrected in the same manner as described above, the same effects can be attained. However, when the moisture layer is appeared on the window of the air adapter, the error is occurred even if anti-fogging film is used as windows of airway adaptor, since the absorption of infrared radiation in the two wavelengths with respect to the water are different. Thus, in order to eliminate this phenomenon, there is required the heater to avoid the condensation of water vapor on the surface of the windows. In this point, this technique is quite different from the two embodiments of the present invention described above.

What is claimed is:

1. A gas analyzer comprising:
    a light source for intermittently generating infrared radiation;
    first signal outputting means having a first photoconductive infrared detector for outputting an electric signal which corresponds to a resistance of said first photoconductive infrared detector which is irradiated with the infrared radiation from said light source via a gas to be measured;
    second signal outputting means having a second photoconductive infrared detector for outputting an electric signal which corresponds to a resistance of said second photoconductive infrared detector which is irradiated with the infrared radiation from said light source via said gas to be measured;
    a gas cell filled with a gas that is the same as the gas to be measured, said gas cell being located between said light source and one of said first signal outputting means and said second signal outputting means such that infrared radiation passes through said gas cell;
    AC component detecting means for detecting an AC component from the output signal of said first and second signal outputting means;
    DC component detecting means for detecting a DC component from the output signal of at least one of said first signal outputting means and said second signal outputting means when said light source does not generate said infrared radiation;
    storage means for storing data specific to said first and second photoconductive infrared detectors, said data relating to the resistance and a sensitivity; and
    correcting means for correcting the AC component detected by said AC component detecting means, based on the data stored in said storage means and the DC component from the output signal of at least one of said first signal outputting means and said second signal outputting means.

2. The gas analyzer comprising according to claim 1, further comprising:
    gas concentration calculation means for calculating a concentration of the measurement gas, based on said AC component corrected by said correcting means.

3. The gas analyzer according to claim 2, wherein said measurement gas contains carbon dioxide.

4. The gas analyzer according to claim 1, wherein said first and second photoconductive infrared detector is a lead selenide (PbSe) detector.

5. The gas analyzer according to claim 1, wherein said DC component detecting means comprises an operational amplifier and a resistance, wherein an inverting input terminal and an output terminal of said operational amplifier are connected to each other via said resistance, and the DC component is outputted as the voltage of said resistance.

6. A method for measuring a concentration of a measurement gas comprising the step of:

intermittently generating infrared radiation;

outputting an electric signal which corresponds to a resistance of a first photoconductive infrared detector which is irradiated with the infrared radiation from a light source via a measurement gas;

outputting an electrical signal which corresponds to a resistance of a second photoconductive infrared detector which is irradiated with the infrared radiation from a light source via a measurement gas and gas cell filled with a gas including the same as a gas to be measured;

detecting AC and DC components from the electrical signal of said first and second photoconductive infrared detectors, said DC components detected when said infrared radiation is not generated; and correcting the detected AC components, based on the data specific to said first and second photoconductive infrared detectors and said detected DC component of the electric signal.

7. The method of measuring a concentration of a measurement gas according to claim 6, further comprising the steps of:

calculating a concentration of the measurement gas, based on the AC components corrected by said correcting step.

8. A gas analyzer comprising:

a light source for intermittently generating infrared radiation;

first signal outputting means having a first photoconductive infrared detector for outputting an electric signal which corresponds to a resistance of said first photoconductive infrared detector which is irradiated with the infrared radiation from said light source via a gas to be measured;

second signal outputting means having a second photoconductive infrared detector for outputting en electric signal which corresponds to a resistance of said second photoconductive infrared detector which is irradiated with the infrared radiation from said light source via said gas to be measured;

restraining means for restraining change of output of said second signal outputting means to be small even when a concentration of gas to be measured in changed largely;

AC component detecting means for detecting an AC component from the output signal of said first and second signal outputting means;

DC component detecting means for detecting a DC component from the output signal of at least one of said first signal outputting means and said second signal outputting means when said light source does not generate said infrared radiation;

storage means for storing data specific to said first and second photoconductive infrared detectors, said data relating to the resistance and a sensitivity; and correcting means for correcting the AC component detected by said AC component detecting means, based on the data stored in said storage means and the DC component from the output signal of at least one of said first signal outputting means and said second signal outputting means.

9. The gas analyzer according to claim 8, wherein said DC component detecting means comprises an operational amplifier and a resistance, wherein an inverting input terminal and an output terminal of said operational amplifier are connected to each other via said resistance, and the DC component is outputted as the voltage of said resistance.

10. A gas analyzer comprising:

a light source for intermittently generating infrared radiation;

signal outputting means having a photoconductive infrared detector for outputting an electric signal which corresponds to a resistance of said photoconductive infrared detector which is irradiated with the infrared radiation from said light source via a gas to be measured;

DC component detecting means for detecting a DC component from the output signal of said outputting means when said light source does not generate said infrared radiation, having an operational amplifier and a resistance, wherein an inverting input terminal and an output terminal of said operational amplifier are connected to each other via said resistance, and the DC component is outputted as the voltage of said resistance;

AC component detecting means for detecting means for detecting an AC component from the output signal of said signal outputting means;

storage means for storing data specific to said photoconductive infrared detector, said data relating to the resistance and a sensitivity; and correcting means for correcting the AC component detected by said AC component detecting means, based on the data stored in said storage means and the DC component of the signal output from said signal outputting means.

* * * * *